United States Patent [19]
Satoh et al.

[11] Patent Number: 4,908,313
[45] Date of Patent: Mar. 13, 1990

[54] PROCESS FOR PRODUCING AMIDES BY USE OF MICROOGANISMS

[75] Inventors: Yoshiaki Satoh; Yasutaka Nakashima; Kanehiko Enomoto; Atsushi Fujiwara; Toshiaki Doi, all of Kanagawa, Japan

[73] Assignee: Nitto Kagaku Kogyo Kabushiki Kaisha, Tokyo, Japan; a part interest

[21] Appl. No.: 131,281

[22] Filed: Dec. 10, 1987

Related U.S. Application Data

[63] Continuation of Ser. No. 627,859, Jul. 5, 1984, abandoned.

[30] Foreign Application Priority Data

Jul. 12, 1983 [JP] Japan ................................. 58-125588

[51] Int. Cl.$^4$ ......................... C12P 13/02; C12N 9/06
[52] U.S. Cl. ..................................... 435/129; 435/191
[58] Field of Search ......................................... 435/129

[56] References Cited

U.S. PATENT DOCUMENTS 3,880,717  4/1975  Rubin et al. ........................ 435/173

FOREIGN PATENT DOCUMENTS 2132201  11/1972  France .
0048889   5/1981  Japan ................................... 435/129
 417863  10/1934  United Kingdom .
2018240  10/1979  United Kingdom .
2048877  12/1980  United Kingdom ................ 435/129

OTHER PUBLICATIONS

Hug et al., Journal of Bacteriology, 102, 874–876 (1970).
Hug et al., Photochemistry and Photobiology, 13, 171–177 (1971).
Hug et al., Biochemistry, 10, 1397–1401 (1971).
Hug et al., Journal of Biological Chemistry, 253, 7622–7629 (1978).

Primary Examiner—Joseph A. Lipovsky
Attorney, Agent, or Firm—Emmanuel J. Lobato; Robert E. Burns

[57] ABSTRACT

In a process for hydrating a nitrile compound by the action of a microorganism having nitrilase activity to convert the nitrile compound into the corresponding amide compound, the performances such as yield and reaction velocity are markedly enhanced by irradiation of the microorganism with light. The process of the present invention is characterized in that (a) the microorganism having nitrilase activity is a positive gram-staining microorganism, (b) the microbial cells are allowed to accept light energy of at least about $1 \times 10^{-2}$ $\mu$E/g microbial cells second before termination of the hydration reaction, and (c) the hydration reaction is carried out in a vessel composed at least partly of a non-light transmitting material.

11 Claims, No Drawings

PROCESS FOR PRODUCING AMIDES BY USE OF MICROORGANISMS

This is a continuation of application Ser. No. 627,859, filed Jul. 5, 1984, now abandoned.

BACKGROUND OF THE INVENTION

1. Field of the Art

This invention relates to a process for hydrating a nitrile compound by the action of microorganisms having nitrilase activity to convert the nitrile compound into the corresponding amide compound. More particularly, this invention relates to the process for producing an amide compound by (irradiation with light of the microorganisms) with good yield, space time yield and productivity per bacterial cells (i.e. the amount of amide compounds to be produced per unit amount of bacterial cells used).

Recently there have been developed processes for carrying out chemical reactions by the use of microorganisms or enzymes obtained therefrom. In general, the reactions by means of microorganisms or enzymes are advantageous in that consumption of energy for the reactions is small because the reaction can be carried out at room temperature and atmospheric pressure and that desired products of high purity are easily obtained because the selectivity of the reaction to yield the desired products is very high. On the other hand, there is room for improvement with respect to the reaction activity, the life time of microorganisms or enzymes used as catalysts. Especially, there are problems when the velocity of the desired reaction (i.e. reaction activity) is low under its optimum conditions and especially at its optimum temperature and/or pH. In such a case, the productivity per bacterial cells used is reduced because large capacity reactors are required owing to low space yield, the reaction takes a longer time owing to a slow reaction velocity, and also the reaction activity is lowered.

Thus, it is fundamentally important to realize a high reaction activity with the microorganisms or enzymes to be used. Such reaction activity is a main economical factor of industrial production.

2. Prior Art

Processes for hydrating nitrile compounds to produce the corresponding amide compounds by the action of microorganisms having enzymatic activity which hydrates a nitrile compound into the corresponding amide compound (i.e. nitrilase activity) are described in Japanese Patent Publication Nos. 17918/81 and 38118/81 and Japanese Laid-Open Patent Application (Kokai) No. 86186/76 Specifications. Microorganisms play an important role in these reactions, and several microorganisms are disclosed in the specifications referred to above.

3. Problems

It has been found by the present inventors that the nitrilase activity cannot be exhibited sufficiently when a large metal reaction apparatus is used in order to carry out hydration reaction of nitrile compounds in an industrial scale by utilizing the nitrilase activity of these microorganisms. It has been uncertain whether these phenomena are caused by the microorganisms themselves or the material and structure of the reaction apparatus or other reasons. Thus it was necessary to solve these problems for industrial operation of a microbiological process for producing amide compounds.

SUMMARY OF THE INVENTION

It is an object of the present invention to solve the above mentioned problems. This object is achieved by irradiation of the microorganisms to be used with light.

According to the present invention, there is presented an improvement in a process for hydrating a nitrile compound by the action of a microorganism having nitrilase activity to convert the nitrile compound into the corresponding amide compound, and the improvement comprises conducting the reaction under the conditions of wherein:

(a) the microorganism having nitrilase activity is positive Gram staining;

(b) the microbial cells are allowed to accept light energy of at least about $1 \times 10^{-2}$ $\mu$E/g microbial cells·second before termination of the hydration reaction, and (c) the hydration reaction is carried out in a vessel composed at least partly of a material which does not permit transmission of light therethrough.

Thus, in the hydration reaction of a nitrile compound by the action of a microorganism having nitrilase activity according to the present invention, (i) the hydration reaction which does not substantially proceed in a reaction vessel composed of a non-light-transmitting material where light is substantially absent can proceed by irradiation of the microorganisms with light, and (ii) the hydration reaction which proceeds to some extent in a reaction vessel composed partly of a non-light-transmitting material where some amount of light is present can proceed substantially faster by the irradiation and light.

This hydration reaction takes place by the action of nitrilase. More specifically, the effect of the light irradiation is realized when the microorganism itself is irradiated with light. Such effects cannot be exhibited when either extracted enzymes or microorganisms having no nitrilase activity are irradiated with light.

It is well known that useful substances are produced according to microbiological methods including the use of enzymes. However, enhancement of the activity of microorganisms or their enzymes by irradiation with electromagnetic waves such as light is not believed to have been known. On the contrary, it is generally believed that the irradiation with light is often harmful. Thus, it can be said that the effect of irradiation with light which is exhibited only in the above mentioned case has not been expected in view of the usual results of light on cases.

DETAILED DESCRIPTION OF THE INVENTION

Microorganisms to be used

As described above, it is known that a nitrile compound is converted to the corresponding amide compound by the action of microorganisms having nitrilase activity. The present inventors have found that the microorganisms belonging to the genuses described in the above mentioned Japanese Patent Publication Nos. 17918/81 and 38118/81 and Japanese Laid-open Patent Application No. 86186/76 Specifications generally have improved activity by the irradiation thereof with light.

It is the common characteristics of the microorganisms belonging to these genuses that (i) the microorganisms have positive Gram-staining property, (ii) they generally contain phospholipid, (iii) their cell membranes are thick and thus exhibit some resistance to the permeation therethrough with substances, and (iv) crushing of the membranes is not easy in order to take out intra-cellular enzymes.

The effect of light irradiation according to the present invention cannot be observed in microorganisms other than those having nitrilase activity as far as tested by the inventors.

It is of interest to note that the light-irradiation effect according to the present invention is not on the nitrilase enzyme itself. More specifically, the enzyme was extracted according to a known method from N-774 bacterial cells of Corynebacterium, which is one of the microorganisms to be used in the present invention, and the resulting enzyme was purified and subjected to measurement of its nitrilase activity. It was found that there was no difference in the enzymatic activity with or without light irradiation.

It is considered according to one theory that the velocity of permeating through the cell membrane of the substrate (nitrile) and product (amide) is enhanced by the irradiation with light, and the apparent activity of nitrilase is thus increased. The present invention should not be bound by such a theory, but it is generally established that the present invention can be applied to the Gram-positive bacteria having resistance to permeation of substances through their cell membranes.

The microorganisms to be used in the present invention are Gram-positive bacteria having nitrilase activity. Specific examples of such microorganisms include the bacteria belonging to the following genuses:
(a) Corynebacterium;
(b) Nocardia;
(c) Bacillus;
(d) Bacteridium;
(e) Micrococcus; and
(f) Brevibacterium.

Specific strains belonging to these genuses include: Corynebacterium—N-771 strain (FERM P 4445 deposited at a Japanese depository, Fermentation Research Institute, Agency of Industrial Science and Technology, 1, 3-Higashi 1-chome, Yatabe-machi, Tsukuba-gun, Ibaraki-ken, Japan, which depository is herein called FRI, on May 30, 1978) and N-774 strain (FERM P 4446 deposited at FRI on May 30, 1978); Nocardi genus—N-775 strain (FERM P 4447 deposited at FRI on May 30, 1978), these strains being described in Japanese Patent Publication Nos. 17918/81 and 38118/81 Specifications; and the strains other than those of Bacillus which are described in Japanese Laid-open Patent Application No. 86186/1976 Specification and reported to have been deposited at FRI. The bacteriological properties of these strains are described in these publicly known specifications.

Nitrile Compounds and Amide Compounds

The nitrile compounds are represented by the general formula $R—(CN)_n$ and encompass broad ranges of compounds. The compounds include mononitriles when $n=1$ and polynitriles when $n \geq 2$. The R is hydrogen or a saturated or unsaturated hydrocarbon residue which has a variety of numbers of carbon atom and also has a straight, branched or cyclic chain. The hydrocarbon residue can further contain amino group, hydroxyl group, a halogen, carboxyl group or other substituents which are compatible with the microorganism used.

As a result of experiments with many nitrile compounds as shown in the following Examples, it has been found that the nitrilase activity is enhanced without exception by the irradiation with light. Thus, it is said that the present invention can be generally established with respect to nitrile compounds.

The resulting hydration reaction product is the corresponding amide compound wherein the CN group of the starting nitrile compound is hydrated into a $CONH_2$ group.

From the viewpoint of usefulness of the products, important at least at present will be the production of acrylamide from acrylonitrile and nicotinic acid amide from cyanopyridine.

Hydration Reaction

It is known to carry out the hydration reaction of a nitrile compound under the action of microorganisms having nitrilase activity. In the present invention, the hydration can be conducted in any desired embodiment so far as the object of the invention is not impaired. It is to be noted that no alteration in the hydration reaction itself has been observed.

The method of the hydration reaction generally comprises contacting the starting nitrile compound with the bacterial cells in a aqueous medium for a predetermined period of time.

The bacterial cells can be in the form of a liquid culture; intact bacterial cells separated from the culture medium, preferably those washed with water; a dried product of the intact bacterial cells; or the intact cells or dried cells supported on or immobilized in a carrier. The preferred form of the bacterial cells are intact cells or those immobilized in an aqueous polymer gel such as crosslinked polyacrylamide gel or crosslinked polyvinyl alcohol.

The concentrations of the substrate (nitrile) and the bacterial cells in the aqueous medium can be suitably selected as described above, and are generally in a concentration of the substrate ranging from about 0.01 to about 5% by weight and in a concentration of bacterial cells ranging from about 0.01 to about 2% by weight. The reaction temperature, reaction pH and other reaction conditions can be determined, depending on the type of the microorganisms to be used. Normally, the reaction temperature is in the range of about 0° to about 20° C., and the pH is in the vicinity of about 7. A suitable buffer agent can be used in order to maintain the pH at a predetermined level.

Incidentally, preparation of the bacterial cells to be used in the hydration reaction is readily conducted by culturing the microorganism under suitable conditions. The bacterial cells separated from a culture medium and used for the hydration reaction are generally under non-proliferating conditions.

Irradiation with Light (1) Light

The irradiation with light is conducted onto the bacterial cells which are in the stage before termination of the hydration reaction. The term "before termination of hydration reaction" means any point of time before termination of the hydration reaction, wherein the termination does not always mean the convertion of 100%. Since the irradiation with light is conducted onto the bacterial cells, the stage before termination of hydration reaction also includes the point of time before contacting the cells with a nitrile compound. Accordingly, the irradiation can be conducted before and/or after contacting bacterial cells with a nitrile compound.

The irradiation can thus be conducted solely before the cells are contacted with a nitrile. When the bacteria cells irradiated with light are contacted with a nitrile compound in the absence of light, however, the effect of enhancing the nitrilase activity by the irradiation with light cannot be continued sufficiently, although the effect is revived by irradiation with light. Thus, in a preferred embodiment of the present invention, the bacterial cells are contacted with a nitrile compound and then irradiated with light. Specifically, the irradiation is conducted, for example, before and after contact of the bacterial cells with a nitrile compound.

The "light" to be irradiated according to the present invention can have any wavelength as far as the effect of irradiation is exhibited. However, as readily understood in view of the light being as a region of electromagnetic waves, the effect is small when the light is in a longer wavelength region emitted from a lower energy atomic level. On the other hand, when the wavelength is too short, its energy is too large and the bacterial cells or the molecules (arrangement) of enzymes will be destroyed. Thus, the bacterial cells will lose their enzymatic activity and finally result in so-called sterilization.

In accordance with the inventors' research in the broad range of wavelength regions, light having a long wavelength over 800 nm has no abnormal effect on bacterial cells, but its effect of enhancing the enzymatic activity is not remarkable. When the light has a short wavelength less than 100 nm, the effect of enhancing the activity can be exhibited in a short period of time, but this results in an unrecoverable decrease in the activity of the cells irradiated. Thus, the light preferred in the present invention has a wavelength of about 100 to about 1,000 nm. Specifically, such light can be obtained, for example, from a light for sterilization in a wavelength range of 200 to 300 nm, a blacklight lamp in a wavelength range of 300 to 400 nm, and a light for general irradiation in a wavelength range of 400 to 800 nm.

The irradiation with light can be carried out with any strength or amount as far as the effect of enhancing the activity is observed. More specifically, the irradiation should be conducted so that the bacterial cells receive light energy of at least about $1 \times 10^{-2}$ $\mu$E/g cells·second, preferably at least about $2 \times 10^{-2}$ $\mu$E/g cells·second. Incidentally, the use of immobilized cells sometimes decreases the reaction velocity by from about $\frac{1}{2}$ to about $\frac{1}{3}$ in comparison with the use of living cells at the same concentration. In this case, the irradiation requires light energy about 2 to 3 times as large as the above mentioned value. As to the light energy, the unit "$\mu$E" is the amount of light energy expressed by E (einstein) $\times 10^{-6}$ which corresponds to the energy of photons equivalent to the numbers of 1 mole molecules. The unit "g cells" is the weight expressed in gram of dried bacterial cells. The "second" is a period of irradiation expressed in second.

The amount of light energy, namely at least ca. $1 \times 10^{-2}$ $\mu$E/g cells·second, is larger than that of the environmental light present in a reaction vessel or other reaction apparatus of an ordinary industrial scale, i.e., larger than that which is given by room light and/or scattered sunlight into a room. More particularly, according to the inventors' experiment, the luminous intensity at industrial production sites is normally about 100 luxes. At such intensity of light, the amount of light energy received by a reaction vessel as large as about 250 liters of capacity will be short of the above defined $1 \times 10^{-2}$ $\mu$E/g cells·second, even when the concentration of bacterial cells is as low as 100 ppm and the upper portion of the reaction vessel is fully exposed to light.

Thus, in industrial production sites, it is difficult to satisfy the required amount of light energy even under the conditions accessible to light. When the irradiation with light is conducted according to the present invention, the room light if any given to the bacterial cells is included in the total amount of the light energy of at least about $1 \times 10^{-2}$ $\mu$E/g cells·second.

In order to obtain the required reaction velocity in the process of the present invention, the irradiation is carried out, for example, for about 1 hour at the lowest light energy of $1 \times 10^{-2}$ $\mu$E/g cells·second.

(2) Irradiation

The irradiation can be conducted in any way, as far as bacterial cells before or in contact with a nitrile compound can successively or intermittently receive the required amount of light energy from a light source for irradiation.

The term "a light source for irradiation of bacterial cells" means a light source placed inside or outside of the reaction apparatus for irradiation of the bacterial cells with light, and also includes some light such as scattered sunlight and/or room light which may come into the reaction apparatus surrounding the reaction apparatus. Incidentally, when one makes the room where a reaction apparatus is installed excessively or extraordinarily bright so that significant light energy from the room light can come into the reaction apparatus, such a light source should be understood as a light source for irradiation according to the present invention.

More specifically, the irradiation with light can be conducted by, for example, (a) a light source placed at an upper space over a vessel containing bacterial cells (i.e. space over bacterial cells or over an aqueous suspension thereof), (b) irradiation through a window equipped at a top, side or bottom portion of the reaction vessel with an outside light source, (c) irradiation by means of a lamp placed within a liquor in the reaction vessel so that the vessel can also be used as a photochemical reactor, and (d) other methods. As necessary and if possible, reaction liquor is taken out of a vessel (especially a reaction vessel) containing bacterial cells, and the liquor containing the cells is then irradiated in another vessel by a method as described above. The vessel for irradiation in this case can, for example, comprise one or more transparent glass tubes.

The effect of light irradiation according to the present invention can be markedly exhibited, when a large reaction vessel of industrial scale is used wherein the incident light energy from an ordinary room light is short of the required amount of light energy. Such a large reaction vessel is normally made of a non-light-transmitting material and especially of a metal material in its substantial portions. In such a non-light-transmitting reaction vessel, the light energy obtained from ordinary illumination through a window or a cover of the vessel is very small. Thus, positive irradiation with light is indispensable. Incidentally, the term "reaction vessel" herein means a portion of reaction apparatus wherein at least major hydration reaction is carried out.

EXPERIMENTATION
EXAMPLE 1

Washed bacterial cells of N-774 strain (Corynebacterium) were prepared by aerobically culturing the strain in a medium (pH 7.2) comprising glucose 1%, peptone 0.5%, yeast extract 0.3%, malt extract 0.3%, and ferric sulfate. 7 hydrate 0.05% and washing the cells obtained with a 0.05 M phosphate buffer. The cells were dispersed in a 0.05 M phosphate buffer (pH 7.7) at a dark place to prepare a dispersion of the cells having a concentration of 3.5 g dried cells/liter. The resulting cell suspension was divided into two portions. One portion thereof was allowed to stand at 0° C. for 4 hours under irradiation at light energy of $1.5 \times 10^{-1}$ µE/g cells·second, using two sets of a 4 W daylight fluorescent lamp (supplied by Tokyo Shibaura Denki K. K., Japan), hereinafter this sample being referred to as "light standing". The other portion thereof was allowed to stand at 0° C. at a dark place for 4 hours, hereinafter this sample being referred to as "dark standing".

By using each of the cell suspension, acrylamide was produced from acrylonitrile and the reaction velocity was studied in view of the amounts of acrylamide thus produced.

In the case of the light standing bacteria, a mixture of the cells 0.088 part (herein the quantity being shown by the weight of dried cells), acrylonitrile 1 part and 0.05 M phosphate buffer (pH 7.7) 98.912 parts was subjected to reaction at 10° C. in a 50 ml glass reactor under stirring for 20 minutes under the same irradiation condition as described above, hereinafter this reaction being referred to as "irradiated reaction". In the case of the dark standing bacteria, the above mentioned reaction was repeated except that light was not applied, hereinafter this reaction being referred to as "dark reaction". After the termination of the reaction, acrylamide contained in each of the reaction-liquor whose reaction had been terminated was subjected to quantitative analysis by gas chromatography. As a result, the amount of acrylamide (hereinafter referred to as AA) per unit bacterial cells was 41.1 µ mol AA/mg cells·minute in the light standing-irradiated reaction, and 0.34 µ mol AA/mg cells·minute in the dark standing-dark reaction, respectively. The ratio of these production performances was light standing-light irradiated reaction/dark standing-dark reaction = 121.

In the following examples, the value of 41.4 µ mol AA/mg cells·minute obtained by the light standing-irradiated reaction of Example 1 is shown by a relative value of 100 U. Thus, the value obtained by the dark standing-dark reaction of Example 1 amounts to 0.83 U.

EXAMPLES 2 THROUGH 13

The reaction liquor having composition shown in Table 1 was prepared by using each of the light standing and dark standing bacterial cells prepared as in Example 1. The reaction liquor was subjected to reaction as in Example 1. The corresponding amide compounds contained in the reaction-terminated liquor were subjected to quantitative analysis by gas chromatography to obtain the results shown in Table 2, respectively.

TABLE 1

| Example Nos. | Bacteria cells (part) | Starting nitrile (part) | 0.05 M phosphate buffer (part) | pH |
|---|---|---|---|---|
| 2 | 0.088 | acetonitrile (1) | 98.912 | 7.7 |
| 3 | " | methacrylonitrile (1) | 98.912 | " |
| 4 | " | valeronitrile (0.25) | 99.662 | " |
| 5 | " | cyanopyridine (1) | 98.912 | " |
| 6 | " | benzonitrile (0.125) | 99.787 | " |
| 7 | " | propionitrile (1) | 98.912 | " |
| 8 | " | n-butyronitrile (1) | 98.912 | " |
| 9 | " | malononitrile (1) | 98.912 | " |
| 10 | " | succinonitrile (1) | 98.912 | " |
| 11 | " | fumaronitrile (1) | 98.912 | " |
| 12 | " | chloroacetonitrile (1) | 98.912 | " |
| 13 | " | β-hydroxypropionitrile (1) | 98.912 | " |

TABLE 2

| Examples | Starting nitrile compound | Amido compounds produced | Light standing-irradiated reaction (U) | Dark standing-dark reaction (U) | Light standing-irradiated reaction/dark standing-dark reaction |
|---|---|---|---|---|---|
| 2 | acetonitrile | acetoamide | 20.6 | 2.0 | 10.3 |
| 3 | methacrylonitrile | methacrylamide | 82.2 | 1.8 | 45.7 |
| 4 | valeronitrile | valeramide | 14.2 | 0.7 | 20.2 |
| 5 | cyanopyridine | nicotinamide | 16.4 | 5.6 | 2.9 |
| 6 | benzonitrile | benzamide | 12.3 | 0.7 | 17.6 |
| 7 | propionitrile | propioamide | 102.0 | 3.5 | 29.4 |
| 8 | n-butyronitrile | n-butylamide | 220.0 | 5.7 | 38.9 |
| 9 | malononitrile | malonamide | 119.0 | 4.1 | 29.0 |
| 10 | succinonitrile | succinamide | 343.0 | 10.2 | 33.6 |
| 11 | fumaronitrile | fumaramide | 61.1 | 1.5 | 40.7 |
| 12 | chloroacetonitrile | chloroacetamide | 289.0 | 6.5 | 44.5 |
| 13 | β-hydroxypropionitrile | β-hydroxypropioamide | 56.4 | 9.0 | 6.3 |

EXAMPLES 14 THROUGH 18

Washed bacteria cells were obtained by preparing as in Example 1 the strains of the following genuses: Bacillus (CBS-494) in Example 14, Bacteridium (CBS-496) in Example 15, Micrococcus (CBS-497) in Example 16, Brevibacterium (CBS-717) in Example 17, and Nocardia (N-775) in Example 18. The strains having CBS numbers are those deposited at and obtained from Centraal Bureau voor Schimmelcultures (CBS) at Osterstraat 1, Baarn, Netherlands. The washed cells were treated as in Example 1 to obtain light-standing and dark-standing cells. By using the cells in the following formulation, acrylamide was produced from acrylonitrile and the reaction velocity was studied in view of the amounts of acrylamide thus produced.

In the case of the light-standing strains, a mixture of cells 0.088 part, acrylonitrile 1 part and 0.05 M phosphate buffer (pH 7.7) 98.912 parts was subjected to reaction under stirring at 10° C. for 20 minutes (irradiated reaction). In the case of the dark-standing strains, the reaction was repeated except that light was not applied (dark reaction). Acrylamide contained in each of the reaction-terminated liquor was subjected to quantitative analysis by gas chromatography to obtain the results shown in Table 3.

TABLE 3

| Examples | Genuses of bacteria used | Strains | Light standing-light irradiation reaction (U) | Dark standing-dark reaction (U) | The light reaction/the dark reaction |
|---|---|---|---|---|---|
| 14 | Bacillus | CBS-494 | 57.0 | 21.8 | 2.6 |
| 15 | Bacteridium | CBS-496 | 108.4 | 59.6 | 1.8 |
| 16 | Micrococcus | CBS-497 | 61.8 | 27.5 | 2.2 |
| 17 | Brevibacterium | CBS-717 | 106.8 | 1.7 | 62.8 |
| 18 | Nocardia | N-775 | 33.0 | 2.7 | 12.0 |

EXAMPLES 19 THROUGH 21 & COMP. EXAMPLES 1 AND 2

Washed bacterial cells of N-774 strain were prepared by aerobically culturing the strain in a medium (pH 7.2) comprising glucose 1%, peptone 0.5%, yeast extract 0.3%, malt extract 0.3% and ferric sulfate·7 hydrate 0.05% and by washing the cells obtained with a 0.05 M phosphate buffer. The cells were dispersed in 0.05 M phosphate buffer (pH 7.7) at a dark place to prepare 22.72 mg/m liter of the bacterial liquor.

One (1) m liter each of the cell suspension was taken into 50 m liter steel vessels, and 24 m liter each of 0.05 mol phosphate buffer (pH 7.7) was added thereto. The resulting cell suspension was irradiated with a light source used in Example 1 at 0° C. for 1 or 20 hours, wherein the light energy was controlled as shown in Table 4 by use of a filter having different optical areas placed at an upper portion of the vessel.

To each of the cell suspension irradiated with light was added 25 ml of a 5% acrylonitrile solution (in 0.05 mol phosphate buffer solution, pH 7.7). The mixture was subjected to reaction for 20 minutes under the same condition of light irradiation. For comparison, reactions were carried out in the same way by using the cell suspension without light irradiation or by irradiation with light energy lower than $1 \times 10^{-2}$ μ E/g cells·second.

The quantity of acrylamide contained in these reaction liquors was subjected to quantitative analysis by gas chromatography to obtain a reaction velocity. The results are shown in Table 4.

TABLE 4

| Examples or Comparative Examples | | Light energy applied (μE/g bact. body · sec.) | Reaction velocity after irradiation for 1 hour (U) | Reaction velocity after irradiation for 20 hours (U) |
|---|---|---|---|---|
| Examples | 19 | $1 \times 10^{-2}$ | 7.8 | 9.7 |
| | 20 | $2 \times 10^{-2}$ | 13.4 | 17.0 |
| | 21 | $1 \times 10^{-1}$ | 31.6 | 34.0 |
| Comparative Examples | 1 | 0 | 0.29 | 0.29 |
| | 2 | $5 \times 10^{-3}$ | 2.4 | 3.6 |

EXAMPLE 22

Washed bacterial cells of N-774 strain were prepared by aerobically culturing the strain in a medium (pH 7.2) comprising glucose 1%, petone 0.5%, yeast extract 0.3%, malt extract 0.3% and ferric sulfate.0.7 hydrate 0.05%, and by washing the cells obtained with a 0.05 phosphate buffer. Then, 40 parts of the cells prepared (water content 75%), acrylamide 4.5 parts, N,N'-methylenebisacrylamide 0.5 part and 0.05 M phosphate buffer (pH 7.7) 40 parts were mixed into a uniform suspension. Thereto were added an aqueous solution of 5% dimethylaminopropionitrile 5 parts and an aqueous solution of 2.5% potassium persulfate 10 parts. The mixture was subjected to polymerization at 10° C. for 30 minutes. The resulting lump gel containing bacterial cells was crushed into small particles, and the particles were fully washed with 0.05 M phosphate buffer (pH 7.7) to obtain 100 parts of immobilized bacterial cells. The immobilized cells were treated with 0.05 M phosphate buffer (pH 7.7) to obtain liquor of a concentration of 3.5 g dried cells/liter. The liquor of the immobilized cells was divided into two portions. One portion thereof was allowed to stand at 0° C. for 4 hours under the same light irradiation condition as in Example 1 (light standing), and the other portion thereof was allowed to stand at 0° C. at a dark place for 4 hours (dark standing).

By using the immobilized cells in the following formulations, acrylamide was produced from acrylonitrile, respectively. The reaction velocity was studied in view of the amounts of acrylamide thus produced. In the case of the light standing bacteria, a mixture of the immobilized cells gel 0.5 part, acrylonitrile 2.5 parts and 0.05 M phosphate buffer (pH 7.7) 97 parts was irradiated with light under the above mentioned condition and subjected to reaction at 0° C. under stirring for 20 minutes (irradiated reaction). In the case of the dark standing bacteria, this reaction was conducted except that light was not applied (dark reaction).

Acrylamide contained in each of the reaction-terminated liquor was subjected to quantitative analysis by gas chromatography. As a result, the velocity of the light standing-irradiated reaction was 20.0 U, that of the dark standing-dark reaction was 0.4 U, and the ratio of the irradiated reaction/the dark reaction was 50.0.

EXAMPLES 23 AND 24

Immobilized cells of the light-standing N-774 strain were prepared as in Example 22. The resulting immobilized cells 4 parts, acrylonitrile 2.5 parts and 0.05 M phosphate buffer (pH 7.7) 93.5 parts were mixed and placed in a 2.5 liter stainless steel cubic vessel of which the upper portion was opened. The mixture was irradiated in the vessel through the open top surface (144 cm$^2$) with (1) the same light source as used in Example 1 at light energy of $2.48 \times 10^{-2}$ μE/g cells·second or with (2) a 100 W "Cool Beam" light (supplied by Tokyo Shibaura Denki K. K., Japan) at light energy of $1.86 \times 10$ μE/g cells·second, and subjected to reaction at 0° C. under stirring for 20 minutes, respectively. Acrylamide contained in each of the reaction-terminated liquor was subjected to quantitative analysis by gas chromatography. The results are shown in Table 5.

TABLE 5

| Examples | Light energy applied (μE/g cells · second) | Reaction velocity (U) |
| --- | --- | --- |
| 23 | $2.48 \times 10^{-2}$ | 6.7 |
| 24 | $1.86 \times 10$ | 31.9 |

EXAMPLE 25 & COMP. EXAMPLE 3

Immobilized cells of the N-774 strain were prepared as in Example 22. The resulting immobilized cells 0.4 part, an aqueous 0.0025 M sodium sulfate solution 84.6 parts and acrylonitrile 1.8 parts were mixed and placed in a one liter separable glass flask having a portion made non-transmitting for light. The mixture in the flask was irradiated with a 150 W "Cool Light" light (supplied by Tokyo Shibaura Denki K. K., Japan) at a distance of 20 cm apart from the reaction liquor (at light energy of about $7 \times 10^2$ μE/g cells·second) while the pH was controlled with 0.05 N sodium hydroxide solution, and was subjected to reaction while the concentration of acrylonitrile in the reaction system was controlled to 2% by gradually adding 13.2 parts of acrylonitrile. Thus, 100 parts of reaction-terminated liquor was obtained, which contained 20% of acrylamide. The amount of unreacted acrylonitrile was 100 ppm or less 25 hours after starting the reaction.

As a comparative example, the reaction was repeated under the same conditions except that light was not applied. The reaction liquor contained not more than 1% of acrylamide 25 hours after starting the reaction.

REFERENCE EXAMPLE 1

The N-774 strain was cultured and washed as in Example 1. The resulting N-774 cells were crushed at a low temperature by means of a French press to obtain cell suspension. The suspension was subjected to nucleic acid-removing treatment and dialysis to obtain crude enzyme liquor as a 50% ammonium sulfate-saturated fraction, which contained a protein at a concentration of 3.9 mg protein/ml. The liquor was divided into two portions. One portion thereof was allowed to stand at 10° C. for 4 hours under the same light-irradiation condition as in Example 1 (light-standing). The other portion thereof was allowed to stand at 10° C. for 4 hours at a dark place (dark-standing). By using the crude enzyme liquor in the following formulations, acrylamide was produced from acrylonitrile, respectively. The reaction velocity was studied in view of the amounts of acrylamide thus produced.

In the case of the light standing bacteria, a mixture of the crude enzyme liquor 2.5 parts, acrylonitrile 2.5 parts and 0.05 M phosphate buffer 95.0 parts was irradiated with light under the above mentioned conditions and subjected to reaction under stirring at 10° C. for 20 minutes. In the case of the dark standing bacteria, the reaction was repeated under the same conditions except that light was not applied. Acrylamide contained in each of the reaction-terminated liquor was subjected to quantitative analysis by gas chromatography. As a result, the amount of acrylamide (AA) thus produced was 103 μmol AA/mg protein·minute in the light standing-irradiated reaction and 102 μ mol AA/mg protein·minute in the dark standing-dark reaction. The ratio of the irradiated reaction/the dark reaction was 1.01. Thus the effect of the light irradiation was not observed.

REFERENCE EXAMPLE 2

This experiment is to show that a bacterium having no nitrilase activity but having other enzymatic activity is not affected on its enzymatic activity by irradiation with light.

Washed cells of *Brevibacterium ammoniagenes* (IAM 1645) deposited at and obtained from the Institute of Applied Microbiology, University of Tokyo, was prepared by aerobically culturing the strain in a medium (pH 7.2) comprising glucose 2%, sodium fumarate 0.5%, urea 0.2%, monopotassium dihydrogen phosphate 0.2%, magnesium sulfate·7 hydrate 0.05% and corn steep liquor 1%. The cells were dispersed in 0.05 M phosphate buffer (pH 7.7) at a dark place to prepare a suspension of cells having a concentration of 30.0 $OD_{630}$ μm. The bacterial liquor was divided into two portions. One portion thereof was allowed to stand at 30° C. for 1 hour at a distance of 20 cm apart from a 150 W "Cool Beam" light (supplied from Tokyo Shibaura Denki K. K., Japan) at light energy of $7 \times 10^2$ μE/g cells·second (light-standing). The other portion thereof was allowed to stand at 30° C. for 1 hour at a dark place (dark-standing). By using these bacterial liquor in the following formulations, malic acid was produced from fumaric acid. The reaction velocity was studied in comparison with the amounts of malic acid thus produced.

In the case of the light-standing bacterial liquor, a mixture of the above prepared bacterial liquor 50 parts, sodium fumarate 8 parts and 0.05 M phosphate buffer (pH 7.7) 42 parts was reacted with stirring at 30° C. for 1 hour under the above mentioned irradiation condition. In the case of the dark-standing bacterial liquor, the reaction was conducted under the same conditions except that light was not applied. Fumaric acid was precipitated with 2N-HCl and removed from the reaction-terminated liquor, and then malic acid contained in each of the reaction-terminated liquor was determined by the color development method with 2,7-naphthalene diol. As a result, the amount of malic acid was 3.40 μ mol/O.D. hour in the light-standing/irradiated reaction and 3.36 μ mol/O.D. hour in the dark standing-dark reaction. The ratio of the irradiated reaction-the dark reaction was 0.95. Thus the effect of light irradiation was not observed.

It is known that the activity of this bacterium is markedly increased by the treatment with a surfactant. Thus it was tested whether the bacterium treated with a surfactant was affected by light irradiation or not. The cells were treated by suspending the cells cultured as described above in a 1 M sodium fumarate solution (pH 7.5) containing 0.02% cetylpyridium chloride (71.5 $OD_{630}$μm) and subjecting it to shaking at 37° C. for 19 hours. Then, the bacterial cells were separated by centrifugation and washed with 0.05 M phosphate buffer (pH 7.7) to obtain washed cells.

Reactions were carried out as described above by using the treated cells. As a result, the amount of malic acid thus produced was 13.9 μ mol/O.D. hour in the light standing-irradiated reaction and 12.7 μ mol/O.D. hour in the dark standing-dark reaction. The ratio of the light reaction/the dark reaction was 1.09. Thus the effect of light irradiation was not observed.

What is claimed is:

1. In a process for hydrating a nitrile compound by the action of a microorganism having nitrilase activity to convert the nitrile compound into the corresponding amide compound, in which the microorganism having nitrilase activity is contacted with said nitrile in a reaction vessel under conditions which effect the conversion of said nitrile to the corresponding amide, wherein the microbial cells are present in the hydrating medium in a concentration of at least 0.01% by weight, but wherein the amount of environmental light relative to the microbial cells in the reaction vessel is less than $1 \times 10^{-2}$ μE/g·microbial cells·second, the improvement which comprises conducting the reaction under the conditions wherein:
  (a) the microorganism having nitrilase activity is positive Gram staining,
  (b) the microbial cells are allowed to accept light energy having a wavelength of about 100 to about 1000 nm in an amount of at least about $1 \times 10^{-2}$ μE/g·microbial cells·second before termination of the hydration reaction, and
  (c) the hydration reaction is carried out in a reaction vessel which is composed at least partly of a material which does not permit transmission therethrough of light, whereby light energy from the environment of at least $1 \times 10^{-2}$ μE/g·microbial cells ·second is not available in said reaction vessel.

2. The process according to claim 1, in which the microbial cells are allowed to accept light energy in an amount of at least about $2 \times 10^{-2}$ μE/g.·microbial cells·second before the termination of the hydration reaction.

3. The process according to claim 1, in which the irradiation with light is carried out before after contacting the microorganism with the nitrile compound.

4. The process according to claim 1, in which the microorganism belongs to the genus selected from the group consisting of Corynebacterium, Nocardia, Bacillus, Bacteridium, Micrococcus, and Brevibacterium.

5. The process according to claim 1, in which the nitrile compound is selected from the group consisting of acetonitrile, propionitrile, n-butyronitrile, i-butyronitrile, n-valeronitrile, acrylonitrile, methacrylonitrile, benzonitrile, cyanopyridine, malononitrile, succinonitrile, fumaronitrile, chloroacetonitrile, β-hydroxypropionitrile, aminoacetonitrile, and β-aminopropionitrile.

6. The process according to claim 1, in which the vessel is such that at least approximately 5/6 of its surface is composed of a material which does not permit transmission therethrough of light.

7. The process according to claim 1 in which the process is carried out in an aqueous medium containing about 0.01 to about 5% by weight of said nitrile and about 0.01 to about 2% by weight of the microorganism.

8. The process according to claim 1 in which the microorganism is contacted with the nitrile and is then irradiated with light.

9. The process according to claim 1 in which the microorganism is irradiated with light before and after being contacted with the nitrile.

10. The process according to claim 1, in which the microbial cells are present in a concentration of about 0.01 to 2% by weight.

11. The process according to claim 1 in which the hydration reaction is carried out under non-proliferating conditions with respect to the microorganism.

* * * * *